United States Patent [19]
Chen et al.

[11] Patent Number: 5,822,219
[45] Date of Patent: Oct. 13, 1998

[54] SYSTEM FOR IDENTIFYING MATERIALS BY NIR SPECTROMETRY

[75] Inventors: Xiaolin Chen, Beltsville, Md.; Stephen L Monfre, Plainville, Mass.

[73] Assignee: Foss NIRSystems, Inc., Silver Spring, Md.

[21] Appl. No.: 645,104

[22] Filed: May 13, 1996

[51] Int. Cl.⁶ ........................................... G06F 19/00
[52] U.S. Cl. ..................... 364/498; 364/497; 356/303
[58] Field of Search ........................... 364/496, 497, 364/498, 499, 578; 250/339.09, 339.11, 339.12, 340, 341.5, 341.8; 356/303, 306

[56] References Cited

U.S. PATENT DOCUMENTS

| | | |
|---|---|---|
| 4,766,551 | 8/1988 | Begley . |
| 4,885,697 | 12/1989 | Hubner . |
| 5,121,337 | 6/1992 | Brown . |
| 5,121,338 | 6/1992 | Lodder ..................................... 364/498 |
| 5,124,932 | 6/1992 | Lodder . |
| 5,205,701 | 4/1993 | Taylor . |
| 5,223,715 | 6/1993 | Taylor . |
| 5,311,445 | 5/1994 | White . |
| 5,606,164 | 2/1997 | Price et al. ......................... 250/339.09 |

*Primary Examiner*—James P. Trammell
*Assistant Examiner*—M. Kemper
*Attorney, Agent, or Firm*—Lane, Aitken & McCann

[57] ABSTRACT

In a method for identifying an unknown product a library of absorbance spectra of known products is measured and stored in a library. A quick search using clustering techniques is conducted to narrow the search to a few products, followed by an exhaustive search of the spectra of the few products. More specifically, principal component analysis is applied to the absorbance spectra to generate product score vectors extending into principal component inside model space which are divided into clusters and subclusters in accordance with their relative proximity. Hyperspheres are constructed around each vector and an envelope is constructed to enclose each cluster surrounding the hyperspheres within the cluster. The absorbance spectrum of the unknown product to be identified is measured and an unknown product score vector is determined from the unknown product spectrum projecting in principal component inside model space of the clusters. It is determined whether or not the unknown product score vector falls within one of the envelopes and if so the product score vector is projected into the principal component inside model space of that cluster and it is determined whether or not the unknown product score vector falls within any of the subclusters divided from the cluster. This process is repeated until the unknown product score vector is found to lie in a cluster which is not further subdivided. In this manner, the search is narrowed to a few products. An exhaustive search is then carried out to match the spectrum of the unknown product with the spectra of the known products corresponding to the undivided subcluster.

9 Claims, 5 Drawing Sheets

SYSTEM FOR IDENTIFYING MATERIALS BY NIR SPECTROMETRY

BACKGROUND OF THE INVENTION

This invention relates to a system for identifying materials and, more particularly, to a system making use of infrared analysis to match an unknown material with one of a large number of known materials and in this manner identify the unknown material as being the same as the material with which it matches.

Industrial concerns have a need to be able to qualitatively analyze a material to identify the material. For example, when a purchased material has been received, it will normally be identified by labeling and by shipping documents, but these indications are sometimes in error or are missing. By having a system to quickly identify a material when it is received, the material can be identified even if it is mislabeled or the identification of the material is missing before the purchasing company accepts the material and becomes financially responsible for paying for the received material.

Prior to the present invention, infrared analysis had been used to qualitatively identify known materials. One such system making use of infrared analysis is described in U.S. Pat. No. 4,766,551 to Timothy H. Begley issued Aug. 23, 1988. In the system of the Begley patent, the near infrared (NIR) spectrum of a large number of known products are measured by detecting the absorbance of each known product at incremental wavelengths distributed throughout the NIR spectrum. The measurements at each incremental wavelength making up l measurements are considered to be an orthogonal component of a vector extending in l-dimensional space. The spectrum of the unknown material is also measured and is represented by a vector extending in l-dimensional space. The angle between the vector of the unknown product and the vector of each of the known products is calculated and if the angle between the known product and an unknown product is less than a predetermined minimum, the unknown product is considered to be the same as the known product.

The above-described system is reasonably accurate in identifying unknown materials but it takes a substantial amount of time to complete the vector analysis to make the comparison of the unknown product with each known material. Accordingly, this system is not suitable for making a rapid identification of an unknown material such as might be needed on a loading dock.

SUMMARY OF THE INVENTION

The present invention may be considered an improvement on the system described in the Begley patent and makes it possible to identify unknown materials very quickly.

In accordance with the invention, a series of absorbance spectra are measured for a large number of known products. A set of spectra for each known product is determined from different batches of the same product having minor variations, such as might occur from being manufactured by a different process or by having permissible levels of impurities within the product. Each set of spectra comprises absorbance values measured at wavelengths distributed over the near infrared range from 1100 nanometers to 2500 nanometers. The set of spectra for each known product is subjected to principle component analysis to the condense the data representing each product to the order of 10 to 20 values or, more specifically, dimensions. The principle component analysis data compression will result in a set of data which will contain about 90 percent or more of the original set of spectra for a given product. The values of the condensed data for a given product are considered to represent a vector, extending in multidimensional or hyperspace and is referred to as a product score vector. Vectors representing the known products are divided into clusters each consisting of vectors close to one another in the hyperspace in which the vectors extend. The vectors all extend from a common origin in hyperspace and the phrase "position of the vector" refers to the position of the end point of the vector in hyperspace. Accordingly, the closeness of the vectors refers to the closeness of the end points of the vectors. A hypersphere, which is a multi-dimensional sphere, is constructed around the position in hyperspace represented by each known product score vector. The radius of the hypersphere will be a scaler quantity times the Euclidean norm determined from the standard deviation spectrum for the product based on the original set of spectra data obtained for the product. By making the scaler multiplier 3, the hypersphere will encompass the positions of 99 percent of the product vectors of all products which are the same as the known product represented by the product vector at the center of the hypersphere. Following the construction of the hyperspheres around each point in space represented by each known product vector, envelopes are constructed around each group of products which are in the same cluster. These envelopes are preferably defined by rectangular coordinates in hyperdimensional space and, accordingly, correspond to a rectangular parallelepiped in three-dimensional space and may be appropriately termed a hyper-rectangular-parallelepiped. For convenience this structure will be referred to as a hyper-box. Each hyper-box will be defined by a minimum and maximum dimension in each of the n-dimensions of the hyperspace.

The clustering technique initially divides the vectors representing the known products into clusters having different numbers of vectors in a given cluster. For example, some clusters may have as many as 50 vectors contained therein and other clusters may have only 9 or 10 vectors contained therein or less. When the number of vectors within a cluster exceeds a selected number, for example, between 10 and 20, the vectors within that cluster are divided into child clusters or subclusters by applying principal component analysis to the spectra of the cluster. The child clusters are further divided into grandchild clusters or subclusters to define a hierarchial tree of clusters. The division process is carried out until the number of vectors in a given cluster at the most divided level does not exceed the selected number, preferably between 10 and 20. Each of the clusters and subclusters are surrounded by an envelope in the form of a hyper-box. The dimensions of each hyper-box are selected so that it encompasses each hypersphere of each known product vector within the cluster.

When an unknown product is received to be identified, the near infrared spectra of the product is measured yielding absorbance values extending throughout the near infrared range, for example, from 1100 nanometers to 2500 nanometers. This spectral data is processed so as to construct a score vector representing the product, which vector extends in the same space and corresponds to the vectors representing known products. In accordance with the invention, it is first determined whether or not the score vector for the unknown product falls within the envelope of any of the highest order clusters in the hierarchial tree. If the vector of the unknown product falls in a cluster which has subclusters, a score vector of the unknown product is then compared with each of these subclusters at the next level in the hierarchial tree to determine if the vector of the unknown product falls within the envelope surrounding one of the subclusters. If the vector for the unknown product is then determined to fall into a subcluster which is further divided into subclusters, the process is then repeated at the next level down in the hierarchial tree until a score vector of the unknown product is determined to fall into a cluster or subcluster at the lowest level in the hierarchial tree. In this manner, the vector will have been determined to be the same as one of the products in the cluster or subcluster at this lowest level of the hierarchial tree. Since the subcluster or cluster will have at most 10 to 20 products in the cluster, the number of products to which the unknown product will correspond will have been reduced to 10 to 20 products or less. As indicated above, the number of products in the subcluster may be as few as 2 or may be as many as the selected maximum number between 10 or 20. Following the determination of the final subcluster in which the product falls, an exhaustive comparison is made between the spectrum of the unknown product with the spectra and each known product in the final subcluster to determine which product the unknown product corresponds.

At any point during a process if it is determined that the vector of the unknown product does not fall within any cluster or finally to correspond to any product in the final subcluster, the unknown product is considered to be what is known as an outlier and is determined not to correspond to any of the known products.

The clustering technique described above permits a quick search of the spectra in the library of known products to narrow the number of known products to match the unknown product to a few candidate products in the library. After this quick search by the above-identified process, an exhaustive comparison is made of the library spectra representing just those candidate known products, to which the clustering technique narrowed the search, to positively identify the unknown product as matching one of the known products. This exhaustive comparison on the search involves a relatively time consuming comparison of the spectral data of unknown product with sets of spectral data of the known candidate products to which the search has been narrowed by the clustering technique. Because this comparison is with just a few candidate products, the entire identification process is reduced to a small fraction of the time required by the prior art processes to identify a known product. Yet, because an exhaustive comparison is made of the unknown product with the spectra of the candidate products identified by the clustering technique, the accuracy of the identifying process is very high and is equal to that of the prior art processes.

DESCRIPTION OF A PREFERRED EMBODIMENT

Figure 1:
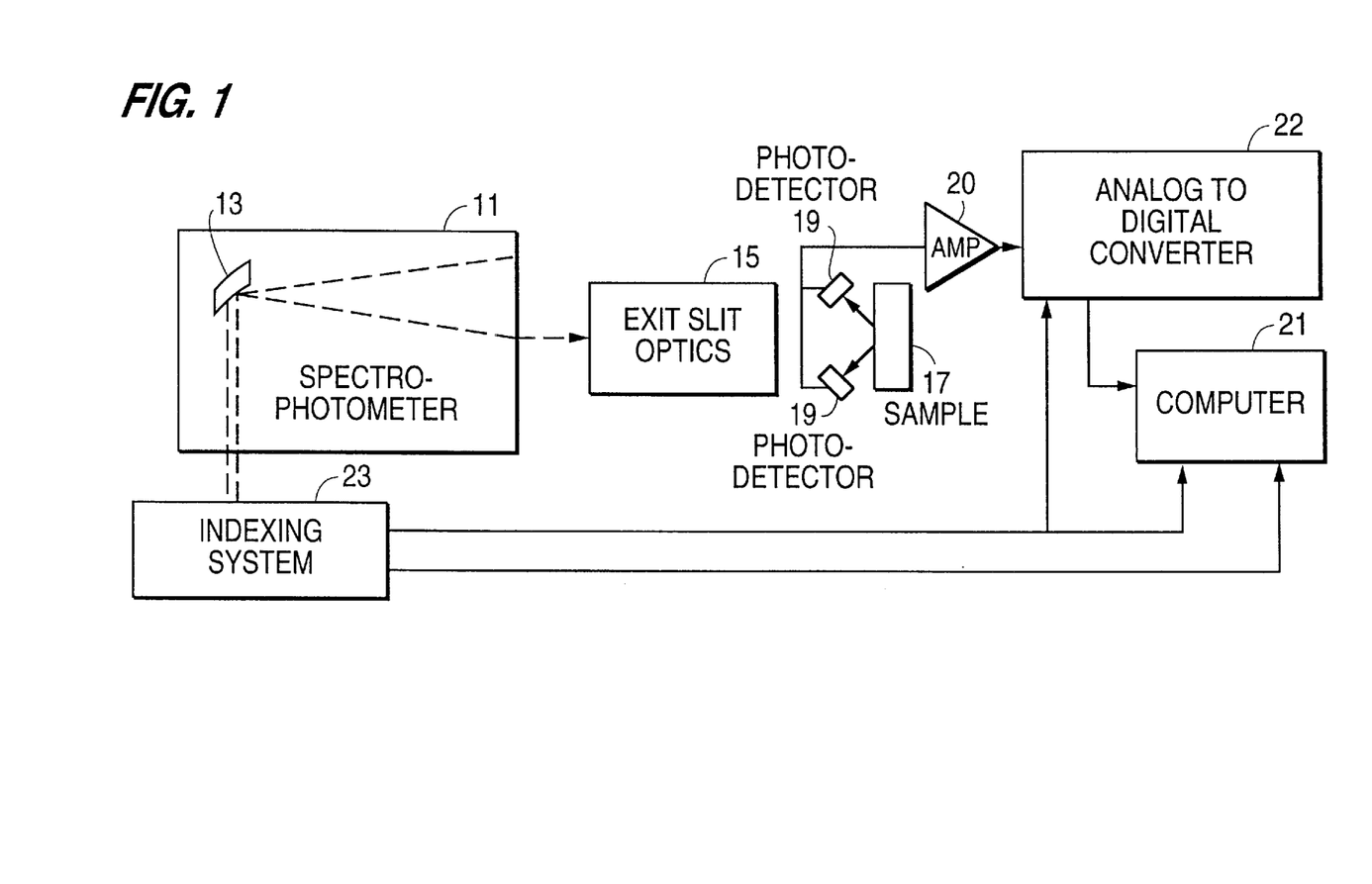
FIG. 1 is a block diagram illustrating the apparatus of the system of the invention.

The apparatus employed in the system of the present invention comprises a near infrared spectrometer 11 having an oscillating grating 13 on which the spectrometer directs light. The grating 13 reflects light with a narrow wavelength band through exit slit optics 15 to a sample 17. As the grating oscillates, the center wavelength of the light that irradiates the sample is swept through the near infrared spectrum. Light from the diffraction grating that is reflected by the sample is detected by infrared photodetectors 19. The photodetectors generate a signal that is transmitted to an analog-to-digital converter 22 by amplifier 20. An indexing system 23 generates pulses as the grating 13 oscillates and applies these pulses to a computer 21 and to the analog-to-digital converter 22. In response to the pulses from the indexing system 23, the analog-to-digital converter converts successive samples of the output signal of the amplifier 20 to digital values. Each digital value thus corresponds to the reflectivity of the sample at a specific wavelength in the near infrared range. The computer 21 monitors the angular position of the grating 13 and accordingly monitors the wavelength irradiating the sample as the grating oscillates, by counting the pulses produced by the indexing system 23. The pulses produced by the indexing system 23 define incremental index points at which values of the output signal of the amplifier are converted to digital values. The index points are distributed incrementally throughout the near infrared spectrum and each correspond to a different wavelength at which the sample is irradiated. The computer 21 converts each reflectivity value to an absorbance of the material at the corresponding wavelength. The structure and operation of a suitable spectrometer is described in greater detail in U.S. Pat. No. 4,969,739.

In accordance with the present invention, the instrument shown in FIG. 1 is used to measure the absorbance spectra from a large number of known products and stores a library of these spectra in its disc memory. The products from which the library of spectra are obtained are selected to be those which will be likely to correspond to an unknown product to be identified by the system of the present invention. The library of the spectra are subjected to principal component analysis using singular value decomposition. The singular decomposition algorithm is used to determine principal component model space in order to reduce the number of values representing the spectrum of each product in the library of products.

In accordance with the invention, several different samples of each product for the library are obtained and each of the different samples of a given product are selected to have minor variations from each other such as would occur from being provided by different manufacturers or being produced by different manufacturing processes.

The system of the invention shown in FIG. 1 is used to measure and obtain an absorbance spectrum of each sample of each product thus providing a plurality of spectra for each product. Each spectrum is measured at the same incremental wavelengths.

The several spectra for the different samples of a product in the library is called a training set. If there are n samples of a given product so that there are n spectra in a training set for a product, then the spectrum of one sample in the training set can be represented as follows:

$$x_i = [x_{i1}, x_{i2}, \ldots x_{il}]^T \qquad (1)$$

in which $x_i$ is a column vector made up of reflectance measurements $x_{i1}$ through $x_{il}$ taken from the sample i at each of the incremental wavelength points 1 through 1. In accordance with the invention, the computer determines a mean spectra from each product training set by averaging the reflectivity values of the training set at each wavelength to thus determine a mean spectra for the product which can be represented as follows:

$$x^m = 1/n(x_1 + x_2 + \ldots + x_n) \tag{2}$$

In the above equation $x^m$ is a column vector of the mean spectrum values and $x_1$ to $x_n$ are each column vectors representing the spectrum of each of the samples 1 through n.

As described in the above-mentioned Begley patent, each known product may be represented by a multi-dimensional vector extending in hyperspace wherein each dimension of the vector is defined as a different one of the absorbance measurements distributed throughout the spectrum. Typically, the near infrared spectrum is measured by 700 incremental measurements distributed throughout the spectrum so that in the system of the Begley patent, each known product will be represented by a 700 dimensional vector.

In the system of the present invention, to reduce the computation required and thereby reduce the amount of time to make the computation to identify the products, the spectra of the products are subjected to principal component analysis. This process reduces the number of numerical values representing each product so that each product may be represented by a vector extending in hyperspace of substantially fewer dimensions, e.g. 10 to 20 dimensions. To carry out the principal component analysis, first a global principal component model space is determined from the mean spectra representing the library of known products. As a first step of this process, the column vectors of the mean spectra are considered to form a matrix X as follows:

$$X = (x^m_1, x^m_2 \ldots x^m_n) \tag{3}$$

In this expression $x^m_1$ through $x^m_n$ each represents a column vector of a mean spectrum for a different one of the products in the product library of known products 1 through n. This expression for the mean spectral matrix of the product library is simplified by dropping the superscript as follows:

$$X = (x_1, x_2, \ldots x_n) \tag{4}$$

From the spectra $x_1$ through $x_n$ a mean column vector $\bar{x}$ is determined by averaging the values in the spectral matrix X at each wavelength. Since X is spectral matrix of mean vectors, the mean vector $\bar{x}$ will actually be a mean vector of a set of mean vectors which is determined from the vectors in the matrix X of Equation 3 as follows:

$$\bar{x} = 1/n(x_1 + x_2 + \ldots x_n) \tag{5}$$

wherein $x_1$ through $x_n$ are mean vectors representing the different products in the spectral library. The vector $\bar{x}$ thus represents an average absorbance at each wavelength from these mean vectors representing the known products. From the global mean vector $\bar{x}$, a mean centered matrix $\bar{X}$ is calculated as follows:

$$\bar{x} = (x_1 - \bar{x}, x_2 - \bar{x}, \ldots, x_n - \bar{x}) \tag{6}$$

Each of the expressions $(x_1 - \bar{x})$ through $(x_n - \bar{x})$ is a column vector and each column vector is determined by subtracting the global mean vector $\bar{x}$ from each of the product mean vectors $x_1$ through $x_n$. Singular value decomposition is then applied to the mean centered matrix $\bar{X}$ to obtain $$\bar{X} = UWV' \tag{7}$$

in which U is an l by n matrix of orthonormal vectors, V' is an n by n matrix of orthonormal vectors and W is an n by n diagonal matrix. The diagonal elements of W are $$w_1 \geq w_2 \geq \ldots w_n \geq 0 \tag{8}$$

and are singular values of $\bar{X}$. The values $w_1$ through $w_n$ are defined as the square root of the eigenvalues of the covariance matrix $\bar{X}' \bar{X}$ wherein $\bar{X}'$ is the transpose of $\bar{X}$. The eigenvalues of the covariance matrix $\bar{X}'\bar{X}$ corresponding to the squares of $w_1$ through $w_n$ are represented as $\lambda_1$ through $\lambda_n$. The principal components of the mean centered spectral data matrix $\bar{X}$ are the eigenvectors of the covariance matrix $\bar{X}' \bar{X}$, which are associated with the nonzero eigenvalues. The column vectors of U in the Expression 7 which are associated with nonzero eigen-values are these eigenvectors and are the principal components for the mean centered spectral matrix $\bar{X}$. Since there are n different mean centered product spectra making up the column vectors of $\bar{X}$, there are n column vectors in the mean centered matrix $\bar{X}$ and there exist n−1 nonzero singular values of $\bar{X}$. Accordingly, there are n−1 principal components of the matrix $\bar{X}$. The Expression 7 can be rewritten in the following standard form in principal component analysis:

$$\bar{X} = LS \tag{9}$$

in which L is an l by n−1 matrix expressed as follows:

$$L = [u_1, u_2 \ldots u_{n-1}] \tag{10}$$

In the matrix L, $u_1$ through $u_{n-1}$ are column vectors and comprise the principal components of the mean centered matrix $\bar{X}$. The matrix L is referred to as the loading matrix.

In Equation (9) S is an n−1 by n matrix called the score matrix and is represented as follows:

$$S = \text{diag}(w_1, w_2 \ldots, w_{n-1})[v_1, v_2 \ldots v_{n-1}]' \tag{11}$$

The principal component vectors of the matrix L span a multidimensional space or hyperspace called principal component model space of the mean centered spectral matrix $\bar{X}$. While as represented in the matrix L, the principal components (vectors) are normalized, the vector lengths are of no significance. It is the direction of the principal components in representing the coordinates of the principal component model space that is significant. Each of the column vectors in the mean centered spectral matrix $\bar{X}$ can be projected in principal component model space and represented as a linear combination of coordinate values.

The magnitude of the eigenvalues $\lambda_1$ through $\lambda_{n-1}$ are proportional to the amount of variance in the mean centered spectral data matrix $\bar{X}$ which are modeled by the corresponding principal components represented by the column vectors $u_1$ through $u_{n-1}$ of the matrix L. The principal components associated with the largest eigen-values model the largest fraction of the total variance in $\bar{X}$. It is possible to model most of the variance in the spectral matrix $\bar{X}$ by substantially fewer than n−1 principal components. The set of nonzero eigenvalues can be partitioned in two sets, a primary set $\lambda_1$ through $\lambda_k$, and a secondary set $\lambda_{k+1}$ through $\lambda_{n-1}$. The primary set includes all values substantially greater than zero so that the secondary set have minimum values substantially equal to zero. The primary set of eigenvalues will cover a large percentage of the cumulative variance of the mean centered spectral matrix $\bar{X}$. In the same way the loading matrix L can be partitioned into $L_I$ and $L_O$ wherein $L_I$ is a matrix made up of the column vectors $u_1$ through $u_k$ called the primary principal components and $L_0$ is a matrix made of the column vectors $u_{k+1}$ through $u_{n-1}$ which are referred to as the secondary principal components. Equation (9) can be rewritten as:

$$\overline{X} = L_I S_I + L_O S_O \qquad (12)$$

In this equation, $S_I$, which is a k by n matrix, can be expressed by following:

$$S_I = \text{diag}(w_1, w_2, \ldots, w_k)[v_1, v_2 \ldots v_k]' \qquad (13)$$

and $S_0$, which is an n-k-1 by n matrix, can be represented as follows:

$$S_O = \text{diag}(w_{k+1}, w_{k+2}, \ldots, w_{n-1})[v_{k+1}, v_{k+2} \ldots v_{n-1}]' \qquad (14)$$

The set of primary principal component vectors represented by $u_1$ through $u_k$ define the orthonormal basis of what is referred to as inside model space of the mean centered spectral matrix $\overline{X}$. The set of secondary principal components represented by $V_{k+1}$ through $v_{n-1}$ define the orthonormal basis of what is defined as outside model space. Each spectrum represented by the column vectors of $\overline{X}$ can be decomposed into the sum of two vectors. The first vector projects in the inside model space and represents the most significant correlated behavior of the vectors in principal component model space, since $w_1$ through $w_k$ covers most of the variance in $\overline{X}$. The second vector projects in outside model space, represents the residual variations in the principal component model space, and is considered to be random error. The second vectors projecting in outside model space are omitted from the analysis because they represent noise and other error terms. The primary principal component vectors $u_1$ through $u_k$ provide an orthonormal basis for K-dimensional inside principal component space which describes most of the variation in the original mean center spectral data matrix $\overline{X}$. The corresponding score matrix $S_I = [S_1, S_2, \ldots, S_n]$ can be computed by $$S_I = L'_I \overline{X} \qquad (15)$$

in which $L'_I$ is the transpose of $L_I$.

The vectors $s_1$ through $s_n$ are each column vectors having k dimensions and are the principal component scores for the corresponding vectors $x_1 - \overline{x}$ through $x_n - \overline{x}$ of the mean centered spectral data matrix in principal component inside model space. In other words, when one of the vectors $x_i - \overline{x}$ is projected in principal component inside model space the values of its coordinates are represented by the column vector $s_i$. The principal component score vector for each mean centered spectrum $(x_i - \overline{x})$ can be directly calculated by $$s_i = L'(x_i - \overline{x}) \qquad (16)$$

The above equation gives a linear transformation in which a spectrum represented by a vector having l dimensions is transformed to a score vector in the principal component inside model space. In this manner, each of the column vectors in this mean centered matrix $\overline{X}$ is transformed into a vector in principal component inside model space having substantially fewer dimensions than the original vector.

Figure 2:
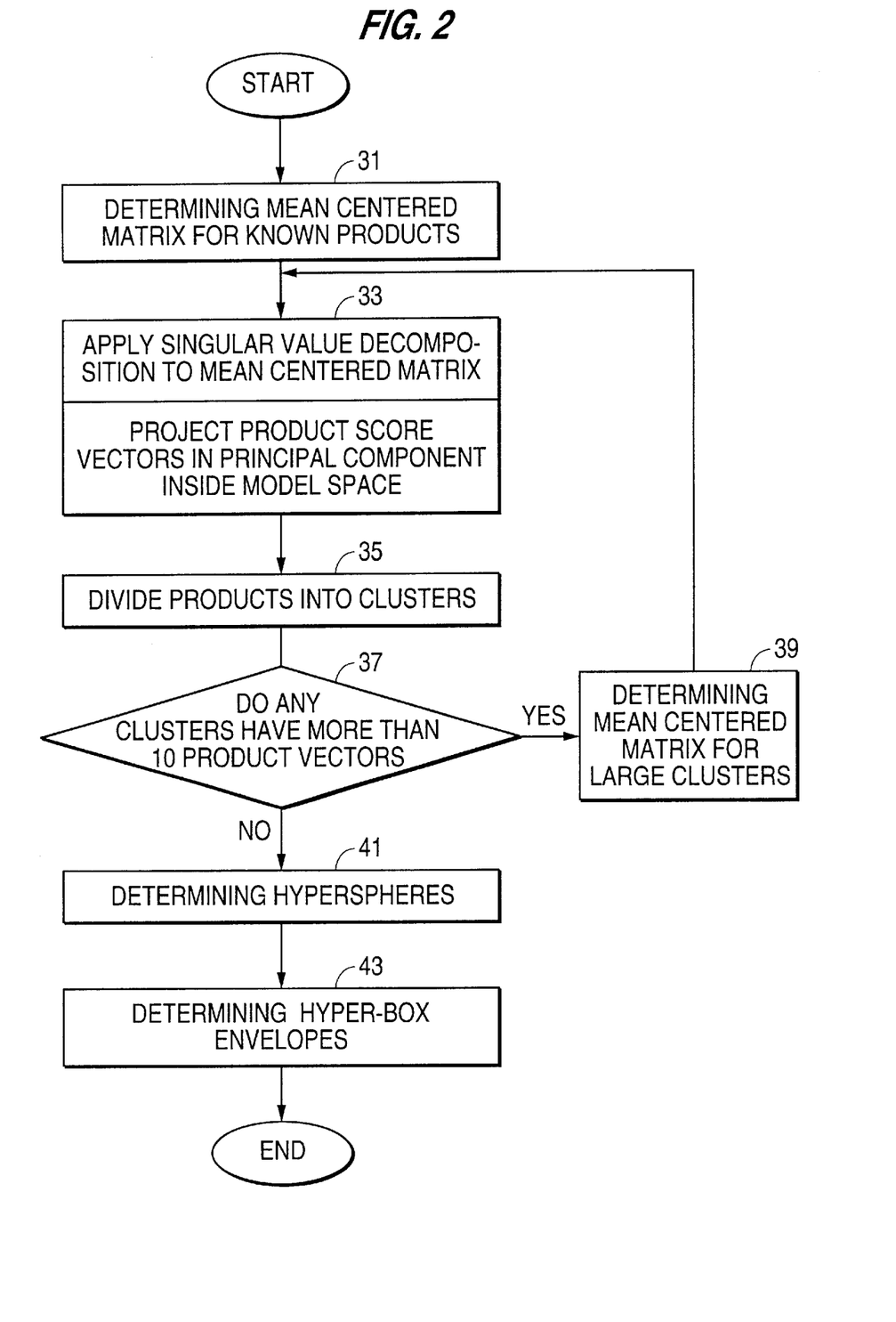
FIG. 2 is a block diagram of the process representing the known products by vectors and dividing the vectors into a hierarchial tree of clusters and subclusters.

Principal component analysis is a known statistical data compression technique and is described in the text entitled *Factor Analysis* by Malinowski. By the process described thus far the entire or global set of mean vectors representing the known products are processed by principal component analysis to yield set of score vectors projected into principal component inside model space. Since each score vector represents a known product, they are referred to as known product score vectors. This process represented in the flow chart of FIG. 2 as step 31 in which the global set of spectra of mean vectors representing known products is transformed into a mean centered matrix $\overline{X}$ and step 33 in which the mean centered matrix is subjected to principal component analysis to yield the known product score vectors for the matrix determined in step 31. These vectors, which each correspond to a different one of the products in the library of products, are then separated into clusters in step 35. To determine which known product score vectors will be in which cluster, the Euclidean distance between the end point of each known product score vector and each other known product score vector is measured and a minimal spanning tree is constructed linking the vectors. The minimal spanning tree is then used to separate the vectors into clusters by dividing the minimal spanning tree at those links of the minimal spanning tree which have the greatest lengths. More specifically, the average length of the minimal spanning tree link is determined and the standard deviation in the length of the minimal spanning tree links is also determined. The minimal spanning tree is then separated into clusters of vectors by defining a cluster separation at each minimal spanning tree link which is greater in length than the average minimal spanning link plus a scaling factor times the standard deviation in the lengths of the minimal spanning tree links expressed as follows:

$$a + \delta,$$

wherein a is the average length of a minimal spanning tree link, k is the scaling factor and $\delta$ is the standard deviation in the length of the spanning tree link.

This process will thus divide the product score vectors from the entire library of products into a set of clusters.

Typically, most of the clusters will contain more than the permitted maximum product score vectors and these clusters are further divided into clusters by repeating the process limited to the products of each cluster. Thus in step 37, if the permitted maximum number of vectors in an individual cluster is 10, it is determined whether any of the cluster have more than 10 vectors. If so, the process proceeds into step 39 in which mean centered matrices are determined for the large clusters containing more than 10 vectors, a separate matrix being determined for each large cluster from the corresponding mean vectors representing the corresponding known products. The process then loops back through step 33 to perform the principal component analysis on the mean centered matrices determined from the large clusters. This process determines a set of principal components for each large cluster to be subdivided and then determines a principal component inside model space for each large cluster. Following this determination the process proceeds again through step 35 to divide vectors of each large cluster into subclusters in the same manner as described above. In this subdivision process, the vectors being subdivided will be closer together than in the first iteration through step 35 so the average length of the minimal spanning tree links between product vectors will be smaller and the criteria for separating the vectors into subclusters will therefore be finer. The principal component analysis as described above is thus carried out to further divide the large clusters containing more than permitted maximum number of product vectors into additional clusters called subclusters or child clusters. In a similar manner the child clusters are then further divided into grandchild clusters, and great grandchild clusters, and great, great grandchild clusters, if necessary, until each cluster or subcluster contains no more than ten products.

Figure 3:
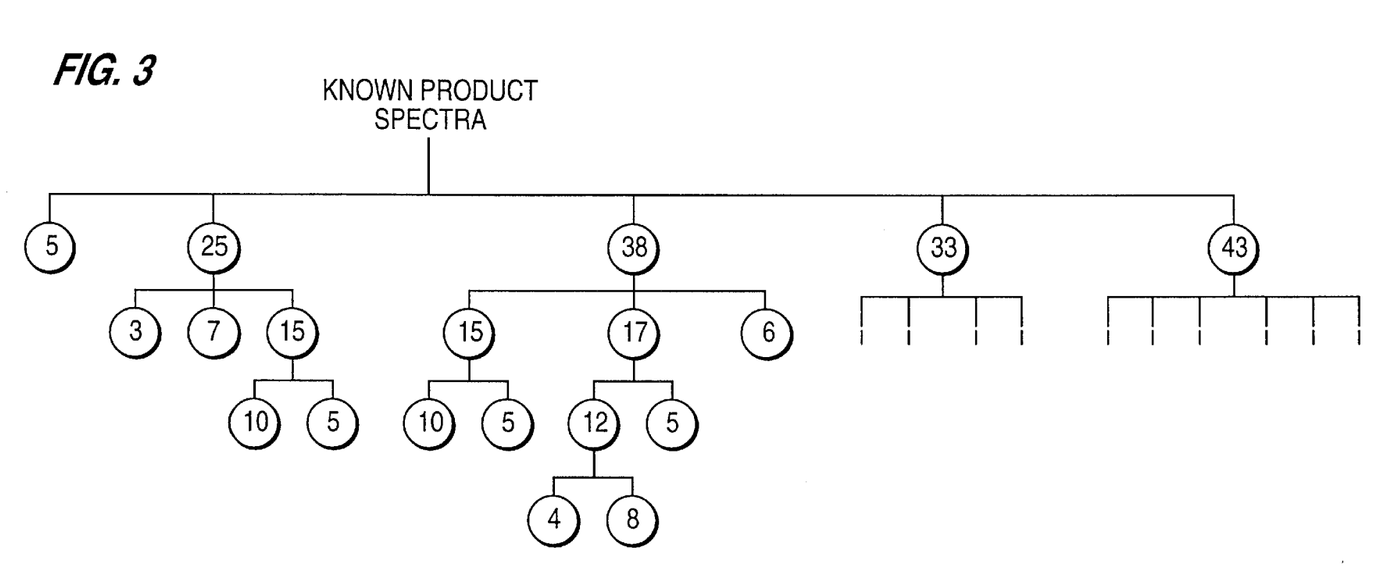
FIG. 3 illustrates an example of how known products might be divided into clusters by the process of the invention.

An example of this clustering technique is illustrated in FIG. 3. In this figure the library of products is assumed to contain 150 known products and in the example illustrated the first division of these products into clusters divides them into a cluster of two, a cluster of 25, a cluster of 38, a cluster of 33, a cluster of nine, and a cluster of 43 products. In this example, the maximum number of vector permitted top be in cluster not to be further subdivided is selected to be ten. The clusters of 25, 38, 33 and 43 having more than ten products need to be divided into further subclusters because they contain more than ten products and accordingly the cluster containing 25 products is divided into subclusters or child clusters which in this example are represented as containing three, seven, and 15 products, respectively. The subcluster containing 15 products is then further divided into subclusters or grandchild clusters containing five and ten products, respectively. The highest level cluster containing 38 products in the example is shown as being divided into subclusters or child clusters containing 15, 17 and seven products, respectively. The child cluster containing 15 products is then further divided into clusters containing ten and five products, respectively, at the third level, and the child cluster containing 17 products is further divided into grandchild clusters containing 12 and five products, and the grandchild cluster of 12 products is further divided into great grandchild clusters containing four and eight clusters at the fourth level. The remaining initial clusters containing 33 and 43 are similarly further divided. In the illustration, the cluster division goes to four levels or great grandchild clusters, but theoretically there is no limit to how many levels the clusters may be further subdivided.

When all of the large clusters have been subdivided into subclusters the process proceeds from step 37 into step 41. In this step a hypersphere is constructed around each vector in each cluster, including the parent clusters as well as the subclusters. The hypersphere will have the same number of dimensions as the principal component inside model space in which it is constructed and therefore will be k-dimensional. The radius of each hypersphere is determined from the Euclidean norm of the standard deviation spectrum of the training set of spectra for the corresponding product multiplied times a scaler factor which may be selected by the user. To calculate the Euclidean norm of the standard deviation spectrum of a training set, the standard deviation is calculated from the training set values at each wavelength measurement point distributed throughout the spectrum and then the Euclidean norm is calculated from these values by taking the square root of the sum of the squares as follows:

$$r = \left( \sum_{i=1}^{l} x_i^{s^2} \right)^{\frac{1}{2}} \quad (17)$$

in which r is the radius and $x_i^s$ is the standard deviation of the training set absorbances at measurement point i. Typically the scaler factor will be selected to be three so that 99% of vectors derived from products corresponding to the product of the training set would be represented by a vector falling within the hypersphere.

Figure 4:
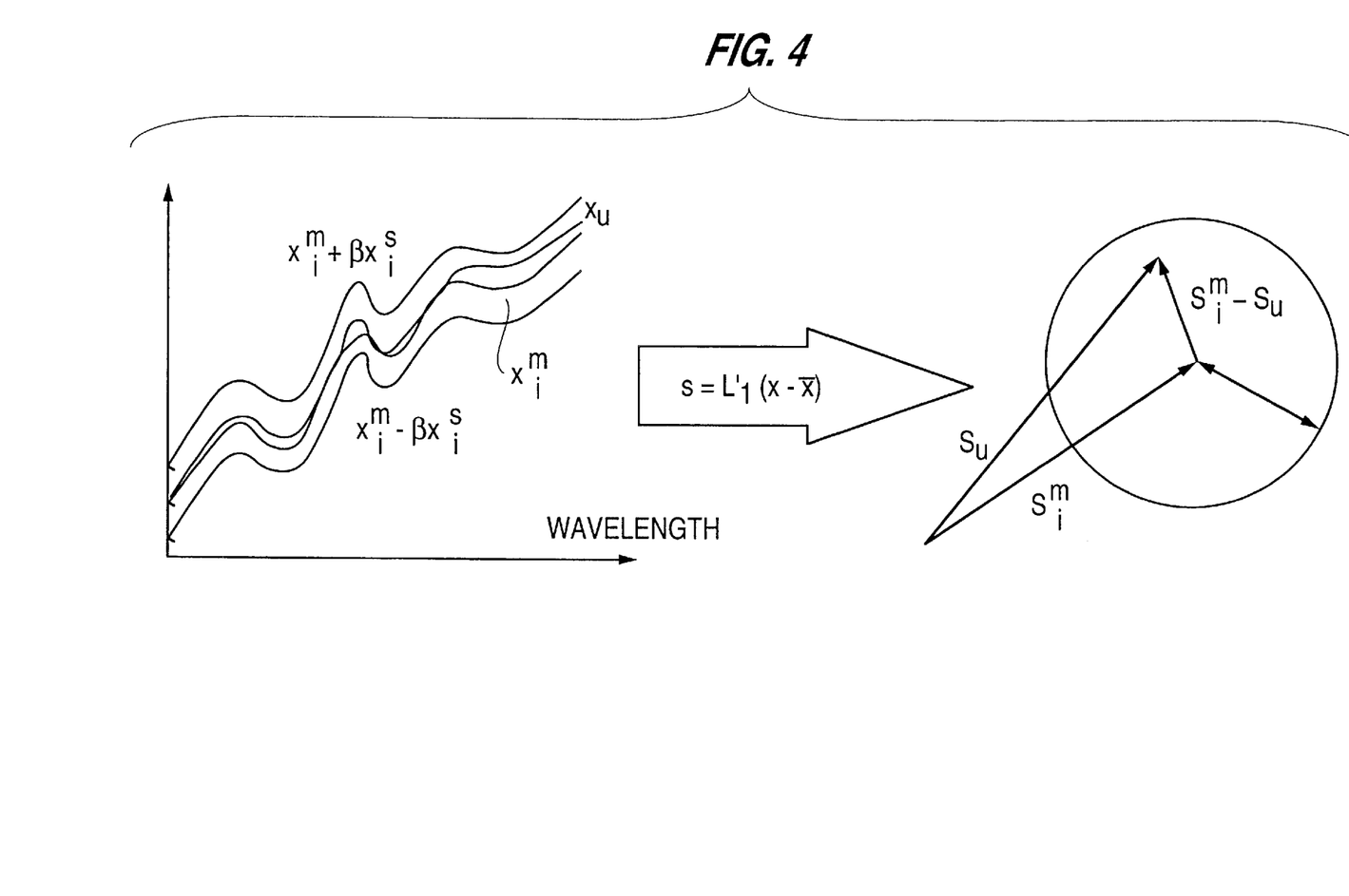
FIG. 4 is a schematic illustration of the process of projecting a product mean and standard deviation spectra into principal component inside model space as a score vector and surrounding the score vector with a hypersphere.

The above described process is illustrated in FIG. 4. In this illustration the product mean spectrum $x_i^m$ yields a mean centered spectrum $x_i - \overline{x}$, which is projected as a product score vector $s_i$ into principal component inside model space by the operation $L'_1(x_i - \overline{x})$. A hypersphere having a radius equal to the Euclidean norm of the standard deviation spectrum of the training set of absorbance spectra for the product multiplied times the scaler factor is constructed around the product score vector $s_i$.

Following the generation of the hyperspheres, envelopes are constructed in step 43 around each cluster of products and each subcluster of products. The envelopes are in the form of multidimensional rectangular boxes called hyperboxes having the same number of dimensions as the principal component inside model space (k dimensions), and will be constructed so as to encompass each of the vector end points and their surrounding hyperspheres.

Figure 5:
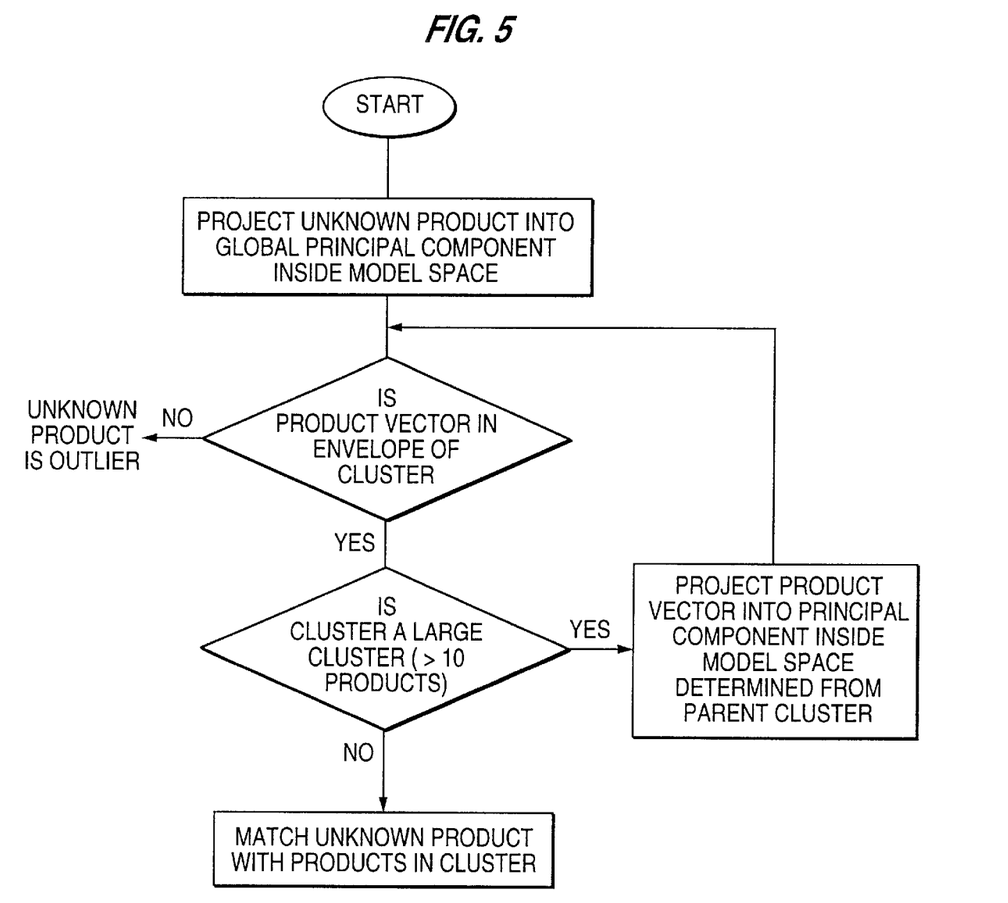
FIG. 5 is a flow chart representing the process of the system of the invention of comparing an unknown product represented by a vector with the clustered vectors of the known products to determine an identification of the unknown product.

The process of identifying an unknown product is illustrated in FIG. 5. In this process, first a quick search of the library known spectra is conducted using the clusters defined as described above. In the quick search, the absorbance spectrum from the unknown product is obtained and a score vector of the resulting spectrum is projected into the principal component inside model space constructed for the global set of clusters in the first step of dividing the clusters. To carry out this projection, first the global mean vector $\overline{x}$ has to be subtracted from the vector representing the unknown product, then the resultant mean corrected vector representing the unknown product is multiplied by the projection operator $L'_I$ wherein $L_I$ and $L'_I$ have been calculated as described above. The projection operator $L'_I$ projects the unknown sample spectrum as a score vector in the principal component inside space spanned by the global principal component vectors. After the projection of the unknown sample into the principal component inside space of the global set of mean vectors, the process determines whether or not the resulting projected product vector representing the unknown product falls within any of the hyperbox envelopes surrounding the clusters. If the vector representing the unknown product falls within the envelope of a cluster, that is one that is not further subdivided, the identification process then proceeds with the exhaustive search comparing the unknown product with each of the products in the cluster, as will be described below.

If the unknown product vector falls in a cluster which is further divided into subclusters, then the above-described process must be repeated for the subclusters to determined which of the subclusters a vector representing the unknown product falls into. As explained above, the principal component inside model space for dividing each cluster into subclusters is different than the global principal component inside model space determined for the global set of mean vectors and also different from that determined for other subclusters. Accordingly, the process of calculating the projection of the unknown product into principal component inside model space must be carried out separately for each subcluster. Thus, in carrying out the projection for given subcluster, the mean vector of the mean centered matrix for the parent cluster will be subtracted from the unknown product vector to determine the mean corrected vector representing the unknown product. Then this mean corrected spectrum vector is multiplied by the projection operator $L'_I$ for the relevant principal component inside model space to project the mean corrected unknown product vector into this principal component inside model space. The relevant principal component inside model space will be that hyperspace used to divide the parent cluster into subclusters. This process is repeated until the vector representing the product is found to fall in a subcluster which is not further divided or otherwise found to fall outside of any subcluster.

When the cluster identification step of the process has been completed and the unknown product is found to fall into an identified cluster or subcluster which is not further divided, an exhaustive search is conducted on the library spectra of those known products of that identified cluster or subcluster to determine which product the unknown product corresponds with. This determination may be carried out by several different methods, one of which is the method described in the above-mentioned patent to Begley wherein the angle between the multidimensional vector represented by the product spectra is compared with the angles of the mean vectors representing the products in the same cluster and if the cosine of the angle between the vectors is less then a certain selected minimum, the product is deemed to be the same product.

A second method is to compare the spectrum of the unknown product point by point with a spectrum band determined from each training set of spectra representing one of the products in the cluster. The spectrum band is determined by calculating the standard deviation of the training set at each wavelength measurement to determine an upper and lower limit for the band at each wavelength. The upper and lower limit is $x_i^m \pm \beta x_s$, in which $x_s$ represents the standard deviation at each wavelength and $\beta$ represents a scaler quantity selected by the user. An example of such a band is illustrated in FIG. 4. The product is determined to be the same as a specific product in the cluster if every point in its absorbance spectrum falls within the band determined from the training set spectra extending over the near infrared of measurement.

In accordance with a third method of performing an exhaustive search of the library spectra of the products corresponding to the cluster identified in the quick search, principal component analysis is applied to each training set of spectra for each product corresponding to the identified cluster. This determination yields a model of principal component inside space for the training set of each product of the cluster. To match the unknown sample with a known product, the score vector from the unknown sample in the local principal component inside model space is determined and the Mahalanobis distance of the score vector and the mean of the score vectors of the training set is calculated. If the Mahalanobis distance of the score vector of the unknown sample is less than the threshold value selected by the user, the unknown sample is determined to match the known sample of the local principal component inside model space. The Mahalanobis distance between the score vector and the mean of the training set score vectors of a known product can be determined from the sum of the squares of the coordinates of the unknown product of the score vector weighted by the associated eigenvalues as follows:

$$d_M^2(s) = (n-1) \sum_{j=1}^{k} (s_j^2/\lambda_j)$$

in which $d_M^2(s)$ represents the Mahalanobis distance, n is the number of samples in the training set, $s_j$ is the $j^{th}$ coordinate of the score vector of the unknown sample, and $\lambda_j$ is the $j^{th}$ eigenvalue associated with the local principal component inside model space derived from the training set of the known product. Geometrically, all score vectors at a Mahalanobis distance smaller than a constant will fall within an ellipsoid boundary in local principal component inside model space centered on the mean of the score vectors of the training set.

Each of the above-described methods of product identification is satisfactory with the first described method of the Begley patent taking the shortest amount of time, the second method taking more time and the third method taking still more time to complete the matching of the unknown product with the known product. Accordingly, in accordance with the preferred embodiment the three methods are carried out in sequence with the method of the Begley patent being used to rule out a first group of the products of the cluster, leaving a remaining smaller group to be considered and then the second method being used to rule out a subgroup of this second smaller group, leaving a third still smaller group to be considered, and then using the Mahalanobis distance method to perform the final matching of the unknown product with a known product in the product library.

As described above, the process employs principal component analysis to reduce the dimensions of the vectors representing both the known products and the unknown products for comparison of the vectors with the clusters of hyperspheres. It will be apparent that the process could be performed without using principal component analysis and simply comparing the mean product vectors representing each product training set by a vector extending in hyperspace having dimensions equal to the number of spectral measurements throughout the infrared range and clustering the products and comparing the unknown products with the cluster of products in the same manner essentially as described above. In addition, other methods instead of principal component analysis may be used to compress the dimensions of the vectors representing each product.

Because the above-described clustering technique is used and also because it is used in combination with the principal component analysis to reduce the number of dimensions of the vectors, the time required to match a product with an unknown product in the library is reduced to a small fraction of the time required by the prior art methods. Accordingly, the system may be used on a loading dock to quickly determine the contents of a received product before a newly delivered product is accepted.

The above description is of a preferred embodiment of the invention and modification may be made thereto without departing from the spirit and scope of the invention which is defined in the appended claims.

We claim:

1. A method of matching an unknown product with one of a library of known products comprising the following steps:

step (1): measuring a near infrared absorbance spectrum for each of said known products, step (2): generating known product vectors extending into hyperspace representing the absorbance spectra determined for each of said known products, step (3): dividing said known product vectors into clusters of vectors extending into hyperspace wherein the end points of the vectors of each cluster are closer to each other in hyperspace than the vectors outside of such cluster, step (4): dividing at least some of said clusters of vectors into subclusters of vectors extending into hyperspace, step (5): repeating said step (4) on at least some of said subclusters until all of said subclusters have fewer than a predetermined number of vectors, step (6): surrounding the end points of the vectors of each of said clusters and subclusters with an envelope defined in the corresponding hyperspace, step (7): measuring the absorption spectrum of said unknown product, step (8): determining in which of said envelopes surrounding said clusters divided in step (3) the end points of a vector, representing said unknown product and extending into the hyperspace of said clusters, falls, step (9): if the end point of a vector representing said unknown product falls into an envelope surrounding a cluster which is divided into subclusters, then determining in which envelope surrounding a subcluster the end point of a vector representing said unknown product and extending into the hyperspace of such subcluster, falls, step (10): repeating the step (9) on further divided subclusters until a vector representing said unknown product is determined to fall into an envelope surrounding a subcluster which is not further divided, step (11): then determining which known product represented by a vector within said last-named envelope said unknown product matches.

2. A method as recited in claim 1 wherein said step (2) includes subjecting said absorbance spectra determined for said known products to principal component analysis to determined a known product score vector representing each known product projected into principal component inside model space.

3. A method as recited in claim 2 wherein said step (4) includes subjecting the absorbance spectra of the known product vectors of each cluster and subcluster to principal component analysis to determined a product score vector for each known product of the cluster or subcluster extending into principal component inside model space determined for the known product spectra of such cluster or subcluster.

4. A method as recited in claim 2 further comprising surrounding the end point of each known product score vector with a hypersphere, said step (6) including surrounding the hyperspheres of the corresponding clusters with each of said envelopes.

5. A method as recited in claim 2 wherein each of said envelopes comprises a hyperbox of orthogonal dimensions.

6. A method as recited in claim 1 further comprising surrounding the end point of each of said known product vectors with a hypersphere, said step (6) including surrounding the hyperspheres of the corresponding clusters with said envelopes.

7. A method as recited in claim 1 wherein each of said envelopes comprises a hyperbox having orthogonal dimensions.

8. A method of matching a product with one of a library of known products comprising measuring the absorbance spectra of said known products, subjecting said absorbance spectra to principal component analysis to determine known product score vectors projecting in principal component inside model space, surrounding the end points of said known product score vectors with hyperspheres, measuring the absorbance spectrum of said unknown product, determining from the spectrum of said unknown product an unknown product score vector projecting in principal component inside model space, and determining in which of said hyperspheres said unknown product score vector falls to thereby determine which known product said unknown product matches.

9. A method as recited in claim 8 wherein said absorbance spectra of said known products includes a training set of a plurality of spectra for each of said known products and wherein said method includes obtaining an average absorbance spectra of each training set, determining from said average spectra and the corresponding training set a standard deviation for each known product, the hyperspheres each having a radius equal to a selected multiple of said standard deviation.

* * * * *

UNITED STATES PATENT AND TRADEMARK OFFICE
CERTIFICATE OF CORRECTION

PATENT NO. : 5,822,219
DATED : October 13, 1998
INVENTOR(S) : Xiaolin Chen et al.

It is certified that error appears in the above-identified patent and that said Letters Patent is hereby corrected as shown below:

Column 1, lines 31, 33 and 35, change "l" to --$\ell$--.
Column 4, line 67, change "$x_{if}$" to --$x_{i\ell}$--.
Column 5, line 1, change "1 through 1" to --1 through $\ell$--.
Column 5, line 61, change Equation (6) to read as follows:

$$\bar{X}=(x_1-\bar{x},\ x_2-\bar{x},\ ...,\ x_n-\bar{x}) \qquad (6)$$

Column 6, lines 3 and 10, change "l" to --$\ell$--.
Column 6, lines 17 and 56, change "eigen-values" to --eigenvalues--.
Column 7, line 6, change Equation (12) to read as follows:

$$\bar{X}=L_1 S_1 + L_0 S_0 \qquad (12)$$

UNITED STATES PATENT AND TRADEMARK OFFICE
CERTIFICATE OF CORRECTION

PATENT NO. : 5,822,219
DATED : October 13, 1998
INVENTOR(S) : Xiaolin Chen et al.

It is certified that error appears in the above-identified patent and that said Letters Patent is hereby corrected as shown below:

Column 7, line 39, change "[S$_1$" to --[s$_1$--.
Column 7, line 56, change "l" to --$\ell$--.
Column 8, line 29, change "a+δ" to --a+kδ--.
Column 9, line 17, change Equation (17) to read as follows:

$$r = (\sum_{i=1}^{\ell} x_i^{s^2})^{\frac{1}{2}}$$

Signed and Sealed this

Sixth Day of June, 2000

Q. TODD DICKINSON

*Attest:*

*Attesting Officer*    *Director of Patents and Trademarks*